Dec. 25, 1945. C. G. DUEHRSEN Plant Pat. 664
ROSE PLANT
Filed Dec. 16, 1944
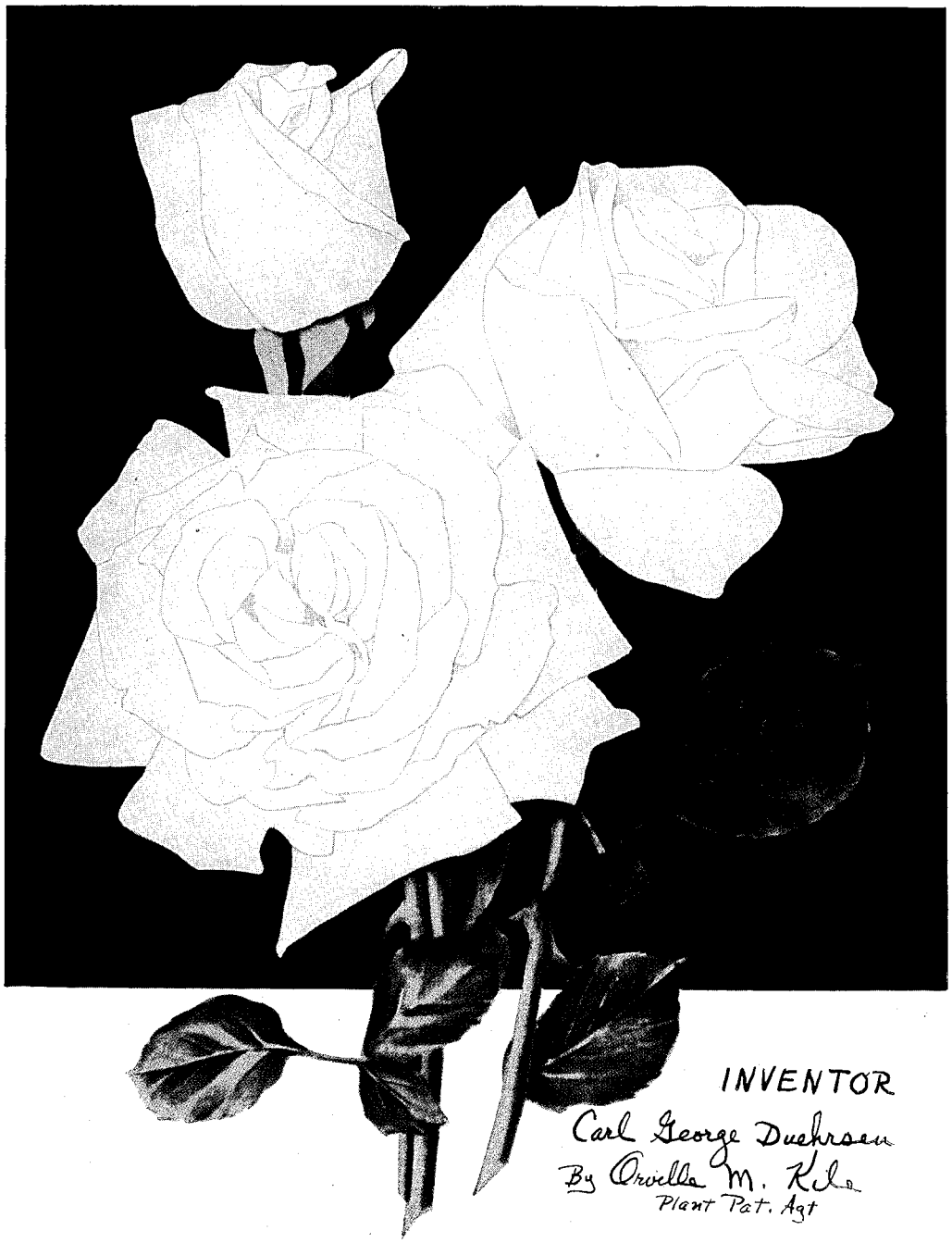

Patented Dec. 25, 1945

Plant Pat. 664

UNITED STATES PATENT OFFICE

664

ROSE PLANT

Carl George Duehrsen, Montebello, Calif., assignor to Howard & Smith, Montebello, Calif.

Application December 16, 1944, Serial No. 568,486

1 Claim. (Cl. 47—61)

My present invention relates to a new and distinct variety of hybrid tea rose plant resulting from definite breeding efforts at Montebello, California. It resulted from a cross between Joanna Hill and Sir Henry Seagrave.

The outstanding features of my new variety are its very strong and vigorous growth and freedom from disease, as well as the distinctive color and form of its blooms. It is notable that during the present very cool season (1944), which is the worst season on record in California and during which many excellent varieties hitherto known to be disease resistant were actually defoliated by mildew and blackspot, the present variety had not a touch of mildew or blackspot.

The illustrations attached to this specification show three specimens of the flowers of this variety in various stages of opening. Reference to color plates indicates Ridgway's Color Standards and Nomenclature.

Following is a detailed description of the plant and flower of my new rose variety:

*Plant*

Growth: Very vigorous and strong grower. Its vigor at least equals that of the variety Charlotte Armstrong.

Form: Upright bush, with an average height of about 4 feet. Makes little lateral growth.

Disease resistance: Extremely resistant to mildew. Grown under the same conditions as Frau Druschki, Charlotte Armstrong, Countess Vandal, and others, during a season when plants of the other varieties were literally defoliated by mildew and blackspot, my new variety had not a particle of mildew or blackspot.

Blooming habit: Constant bloomer, producing blooms freely on long stems.

Stems: Long, rigid; strong; Cerro Green (Plate V) with reddish tinge.

*Thorns.*—Many; large; irregularly grouped; downward pointing; green on main stems, red on new wood.

*Internodes.*—Short; staggered.

Foliage: Leaves are compound, with 3 to 5 leaflets.

*Size.*—Medium; terminal leaflet measuring 2 to 2½ inches long by 1¼ to 1½ inches wide.

*Shape.*—Broad oval with acuminate point.

*Color.*—Forest Green (Plate XVII) on upper surface; approximately Biscay Green (Plate XVII) on under surface.

*Aspect.*—Glossy on upper surface; dull on under surface.

*Substance.*—Leathery; substantial.

*Stipules.*—Clinging and narrow.

*Rachis.*—Heavy; short; grooved and red-tinged above; below, stem green and with several sharp thorns or prickles.

*The Bloom*

Bud:

*Peduncle.*—Short; smooth; straight.

*Sepals.*—Mostly simple; longer than bud when first opening.

*Size.*—About 2¾ inches long.

*Form.*—Long; pointed; conical; perfectly formed.

*Color.*—Strontian Yellow (Plate XVI), with Barium Yellow (Plate XVI) at edges of petals.

Flower:

*Size.*—Typical blooms measure 5 to 5½ inches in diameter.

*Form.*—Loosely built, open form with high center, opening into deep cup-shape. Central petals are much shorter than outer petals.

*Color.*—Barium Yellow (Plate XVI) with base and veinings of Strontian Yellow (Plate XVI), lightening materially toward outer rim of petals. Strontian Yellow to Wax Yellow (Plate XVI) deep within the opening flower.

Petals:

*Texture.*—Substantial.

*Shape.*—Spatulate.

*Arrangement.*—Imbricated.

*Persistence.*—Clinging.

*Petalage.*—Varies considerably but averages around 35.

*Fragrance.*—Delicate.

Reproductive organs:

*Pistils.*—Many; bunched; short. *Styles*—short, greenish white with red tip. *Stigma*—dark yellow.

*Stamens.*—Very many; surround pistils in a tight cluster. Uneven lengths but many of them rise considerably higher than pistils. *Filaments*—Lemon Chrome (Plate IV); long. *Anthers*—Light Cadmium (Plate IV); medium in size. *Pollen*—abundant; pale yellow.

*Comparison*

McGready's Ivory and Sir Henry Seagrave are the varieties most like my new rose variety but differ considerably as indicated below.

My variety is a much stronger, more vigorous grower than either; is very much more disease resistant; and has a better growth habit, producing longer stems and better shaped bush. The buds of my new variety are longer and more perfectly formed. The flowers of my new variety are of looser construction and although its color is more like that of McGready's Ivory than any other rose, it is a more delicate tone of deep lemon-yellow, merging to creamy yellow at outer rim of petals.

Having thus disclosed my invention, I claim:

The new and distinct variety of hybrid tea rose plant substantially as herein shown and described, characterized particularly by its outstanding vigor of growth; its apparently complete resistance to mildew and blackspot; its long, perfectly shaped bud; and its fragrant flowers having a distinctive light yellow color.

CARL GEORGE DUEHRSEN.